(12) United States Patent
Shay et al.

(10) Patent No.: US 11,883,142 B2
(45) Date of Patent: Jan. 30, 2024

(54) SYSTEM AND METHOD FOR CARDIOVASCULAR HEALTH MONITORING

(71) Applicant: ATCOR MEDICAL PTY, LTD., West Ryde (AU)

(72) Inventors: Oliver Hao-Yuan Shay, San Mateo, CA (US); Jessi E. Johnson, Sunnyvale, CA (US); Lillian Lei Dai, Ottawa (CA)

(73) Assignee: ATCOR MEDICAL PTY, LTD., West Ryde (AU)

( * ) Notice: Subject to any disclaimer, the term of this patent is extended or adjusted under 35 U.S.C. 154(b) by 1024 days.

(21) Appl. No.: 16/355,049

(22) Filed: Mar. 15, 2019

(65) Prior Publication Data

US 2019/0282106 A1 Sep. 19, 2019

Related U.S. Application Data

(60) Provisional application No. 62/643,490, filed on Mar. 15, 2018.

(51) Int. Cl.
*A61B 5/024* (2006.01)
*A61B 5/0205* (2006.01)
(Continued)

(52) U.S. Cl.
CPC ............ *A61B 5/02405* (2013.01); *A61B 5/02* (2013.01); *A61B 5/0205* (2013.01);
(Continued)

(58) Field of Classification Search
None
See application file for complete search history.

(56) References Cited

U.S. PATENT DOCUMENTS

| 4,958,638 A | 9/1990 | Sharpe et al. |
| 6,984,993 B2 * | 1/2006 | Ariav ............... G01K 11/22 600/430 |

(Continued)

FOREIGN PATENT DOCUMENTS

| CN | 101371785 A | 2/2009 |
| WO | WO-2015061579 A1 | 4/2015 |
| WO | WO-2019178509 A1 | 9/2019 |

OTHER PUBLICATIONS

Rabbani et al., "Ultra-wide patch antenna array design at 60 GHz band for remote vital sign monitoring with Doppler radar principle", J, Infrared Milli Terahz Waves, 2017, 38:548-566 (published Dec. 2016). (Year: 2016).*

(Continued)

*Primary Examiner* — Yi-Shan Yang
(74) *Attorney, Agent, or Firm* — Andrus Intellectual Property Law, LLP

(57) ABSTRACT

As shown in FIG. 1 and FIG. 2, the health monitoring system 100 of one embodiment includes an electromagnetic transmitter 110 configured to transmit an electromagnetic signal towards a target body region on a user; an electromagnetic receiver 120 configured to receive reflected energy from a target body region on a user; a calibration sensor 130 that measures reference cardiovascular-related parameters of a user (such as vessel pressure, stiffness, or motion); and an activity sensor 140 configured to detect the activity state of a user. The system also includes an attachment mechanism 150 for fixing the electromagnetic transmitter, electromagnetic receiver, calibration sensor and activity sensor to the user; and a stand-off mechanism 160 for fixing the electromagnetic transmitter and electromagnetic receiver at a known standoff distance from a target body region on the user.

16 Claims, 12 Drawing Sheets

(51) Int. Cl.
  *A61B 5/11* (2006.01)
  *A61B 5/00* (2006.01)
  *A61B 5/02* (2006.01)
  *A61B 5/364* (2021.01)
  *A61B 5/05* (2021.01)
  *G01S 13/88* (2006.01)

(52) U.S. Cl.
  CPC ............ *A61B 5/02007* (2013.01); *A61B 5/05* (2013.01); *A61B 5/1118* (2013.01); *A61B 5/364* (2021.01); *A61B 5/681* (2013.01); *G01S 13/88* (2013.01); *A61B 5/0006* (2013.01); *A61B 5/0017* (2013.01); *A61B 5/4809* (2013.01); *A61B 5/742* (2013.01); *A61B 5/747* (2013.01); *A61B 2560/0223* (2013.01)

(56) References Cited

U.S. PATENT DOCUMENTS

| | | | |
|---|---|---|---|
| 8,298,141 | B2 | 10/2012 | Chen et al. |
| 9,134,404 | B2 | 9/2015 | Lee et al. |
| 2006/0094937 | A1 | 5/2006 | Immoreev et al. |
| 2009/0209850 | A1 | 8/2009 | Tao et al. |
| 2010/0179421 | A1* | 7/2010 | Tupin ........................ A61B 5/05 600/426 |
| 2011/0089894 | A1 | 4/2011 | Soar |
| 2012/0010609 | A1 | 1/2012 | Deem et al. |
| 2013/0030257 | A1 | 1/2013 | Nakata et al. |
| 2013/0190599 | A1 | 7/2013 | Wyeth et al. |
| 2014/0062822 | A1 | 3/2014 | Tseng |
| 2014/0343393 | A1 | 11/2014 | Lee et al. |
| 2015/0018676 | A1 | 1/2015 | Barak |
| 2015/0031967 | A1 | 1/2015 | Leboeuf et al. |
| 2015/0073201 | A1 | 3/2015 | Rogachefsky et al. |
| 2015/0109124 | A1* | 4/2015 | He ..................... A61B 5/02028 340/539.12 |
| 2015/0254414 | A1 | 9/2015 | Patel |
| 2015/0359436 | A1 | 12/2015 | Shim et al. |
| 2015/0359463 | A1* | 12/2015 | Matthews ............ A61B 5/7282 600/407 |
| 2016/0228010 | A1 | 8/2016 | Kim et al. |
| 2017/0119318 | A1 | 5/2017 | Shay et al. |
| 2017/0209053 | A1* | 7/2017 | Pantelopoulos ..... A61B 5/7264 |
| 2018/0358686 | A1* | 12/2018 | Park ....................... H01Q 21/08 |
| 2021/0298622 | A1* | 9/2021 | Valenzi .............. A61B 5/14532 |

OTHER PUBLICATIONS

PCT/US2019/022531 International Search Report and Written Opinion dated Jul. 19, 2019.
Rabbani, M.S., et al., Ultr-wide patch antenna array design at 60 GHz band for remote vital sign monitoring with doppler radar principle, J Infrared Milli Terahz Waves, 38: 548-566 (2017).
U.S. Appl. No. 15/337,127, filed Oct. 28, 2016, Abandoned.
U.S. Appl. No. 16/833,421, filed Mar. 27, 2020, Pending.

* cited by examiner

175

| Blood Pressure | Activity Level |
|---|---|
| 140/80 | LOW |
| 150/90 | MEDIUM |
| 170/95 | HIGH |
| 130/80 | SLEEP |

FIGURE 4

SYSTEM AND METHOD FOR CARDIOVASCULAR HEALTH MONITORING

CROSS-REFERENCE TO RELATED APPLICATIONS

This application claims the benefit of U.S. Provisional Application Ser. No. 62/643,490 filed 15 Mar. 2018, which is incorporated in its entirety by this reference.

This application is related to U.S. application Ser. No. 15/337,127 filed 28 Oct. 2016, each of which is incorporated in its entirety by this reference.

TECHNICAL FIELD

This invention relates generally to the biometric field, and more specifically to a new and useful system and method for monitoring cardiovascular health.

BRIEF DESCRIPTION OF THE FIGURES

FIG. 4 is a schematic representation of another embodiment of the invention;

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. A System for Generating a Contextualized Blood Pressure Dataset

Figure 1:
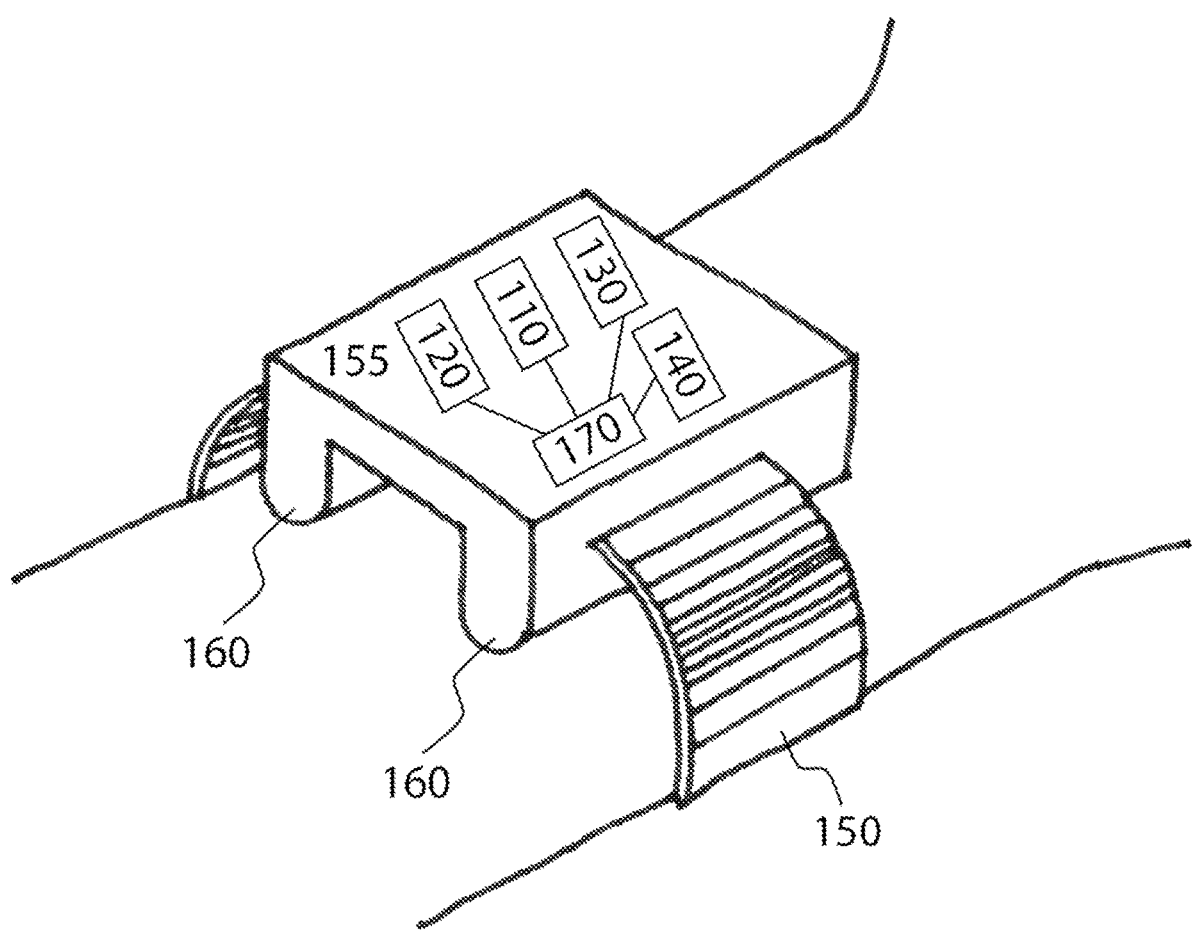
FIG. 1 is a schematic representation of a first preferred embodiment of the invention.
Figure 2:
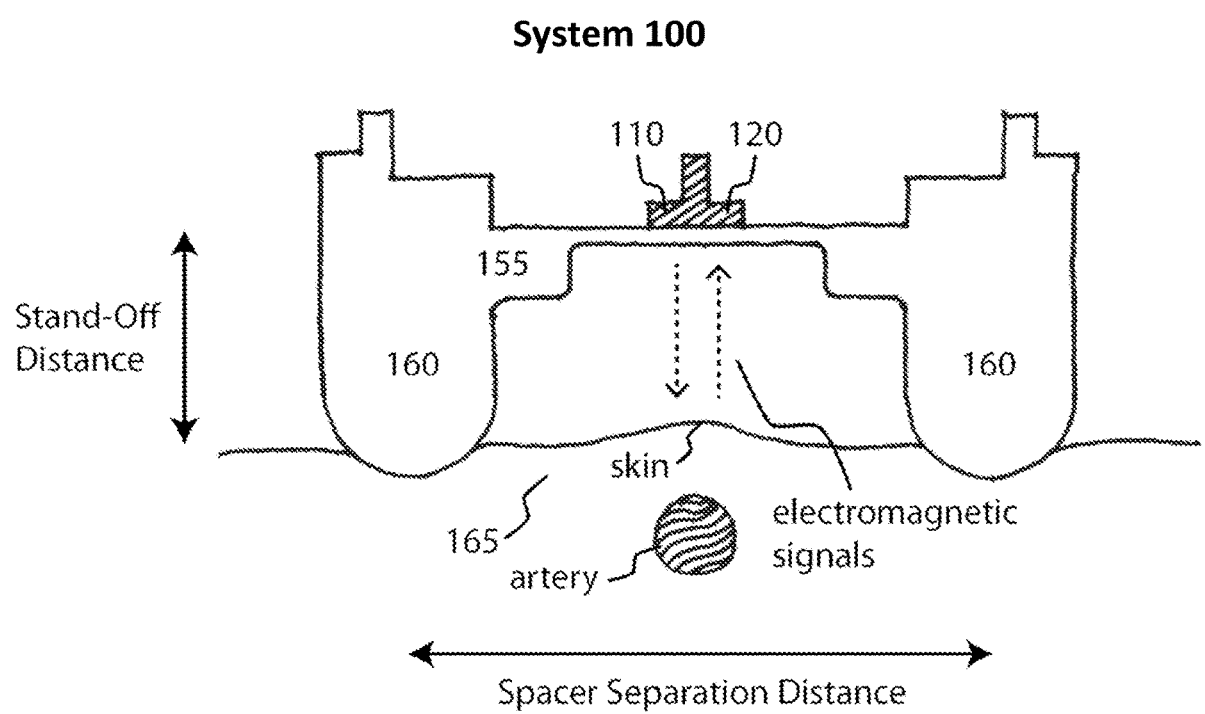
FIG. 2 is a cross-sectional view taken along the line a-b in FIG. 1.

As shown in FIG. 1 and FIG. 2, the health monitoring system 100 of one embodiment includes an electromagnetic transmitter 110 configured to transmit an electromagnetic signal towards a target body region on a user; an electromagnetic receiver 120 configured to receive reflected energy from a target body region on a user; a calibration sensor 130 that measures reference cardiovascular-related parameters of a user (such as vessel pressure, stiffness, or motion); and an activity sensor 140 configured to detect the activity state of a user. The system also includes an attachment mechanism 150 for fixing the electromagnetic transmitter, electromagnetic receiver, calibration sensor and activity sensor to the user; and a stand-off mechanism 160 for fixing the electromagnetic transmitter and electromagnetic receiver at a known standoff distance from a target body region on the user. The standoff ensures that the target body region remains outside of the reactive near-field of the electromagnetic transmitter and electromagnetic receiver. The system also includes a processor 170 which is electrically coupled to the electromagnetic receiver, electromagnetic transmitter, calibration sensor and activity sensor. Processor 170 is configured to evaluate cardiovascular-related parameters of the user based on the received reflected energy. Health monitoring system 100 may also include other components (not shown) such as display, touch screen, battery, power charging unit, wireless communication (e.g. Wi-fi, Bluetooth), GPS, and other peripheral units. In another embodiment, the processor is operable between a calibration mode and an operating mode. In alternative embodiments, either the calibration sensor or the activity sensor or both sensors may be external to the health monitoring system 100. The outputs of the calibration sensor and/or the active sensor may be input into the health monitoring system 100 via wireless communication or manual input. In other embodiments, an external processor (e.g. remote server) may be used to evaluate cardiovascular-related parameters of the user.

The electromagnetic transmitter 110 functions to generate and transmit electromagnetic signals towards a target body region of the user such as an arterial surface pulse; the signals then reflect off of the user and are received by the electromagnetic receiver 120. In one embodiment, the transmit signal is in the millimeter wave frequency band (e.g. between 30 and 300 GHz). In one embodiment, the transmit signals are millimeter-wave signals between 57 and 63 GHz. In one embodiment, the electromagnetic transmitter utilizes frequency modulated continuous wave signals, as would be used for a frequency modulated continuous wave radar system. In another embodiment, the electromagnetic transmitter utilizes fixed continuous wave signals. In another embodiment, the electromagnetic transmitter utilizes pulsed signals. The electromagnetic transmitter can include a transmit antenna subsystem for facilitating radiation of the electromagnetic energy.

The electromagnetic receiver 120 functions to receive reflected signals from the target body region of a user such as an arterial pulse waveform. The timing, shape, phase and amplitude of the received signals will be affected by the arterial pulse waveform, which will in turn enable the determination of the user's blood pressure. In one embodiment, the transmitted and received signals are coupled into the processor 170 to form a radar system. Specifically, the processor may perform mixing, filtering and signal processing of the received signal to extract information related to the position and motion of the target body region of a user. In one embodiment, the radar system is a frequency modulated continuous wave radar system. In another embodiment, the radar system is a continuous wave radar, such as continuous wave doppler radar. In another embodiment, the radar system is a pulsed radar, such as impulse-radio ultra-wideband radar. In one embodiment, only the received signals are coupled into the processor to form the radar system. The electromagnetic receiver can include a receive antenna subsystem for facilitating reception of electromagnetic energy. In one embodiment, transmit and receive functions can be performed with the same antenna subsystem.

The attachment mechanism 150 functions to fix the electromagnetic transmitter and electromagnetic receiver to the user, as well as orient the electromagnetic transmitter and electromagnetic receiver towards a target body region, such as an artery of the user. In one embodiment, the attachment mechanism also functions to fix the calibration sensor to the user. In one embodiment, the attachment mechanism includes an enclosure 155 to house the electromagnetic transmitter and electromagnetic receiver. In one embodiment, the enclosure has geometrical features (such as a thin plastic or open window) that allow minimal perturbation of the transmit and/or receive signal. In one embodiment, the attachment mechanism includes two attachment mechanisms—one fixing the electromagnetic transmitter and electromagnetic receiver to the user and another fixing the calibration sensor to the user. In one embodiment, the attachment mechanism includes a band. Alternatively, the attachment mechanism includes: Velcro, straps, adhesive, silicone, or any other suitable attachment mechanism or combination thereof. In one embodiment, the attachment mechanism is configured to attach to a separate device mounted to the user. In another embodiment, the attachment mechanism is configured to couple the transmitter and receiver to a wearable fitness device. Alternatively, the attachment device is fixed to an exercise machine and enables temporary mounting to a user.

The stand-off mechanism 160 functions to offset the electromagnetic transmitter and electromagnetic receiver at a known stand-off distance from a target body region on the user. This offset positions the enclosure such that the enclosure avoids perturbing the physiology of the target body region and enables the user's skin and tissues overlying the artery to move freely relative to the transmitter and receiver. Alternatively or additionally, the offset maintains the target body region outside of the reactive near-field of the electromagnetic transmitter and electromagnetic receiver, thus preventing unpredictable performance. As shown in FIGS. 1 and 2, in one embodiment, the stand-off mechanism includes two spacers. In one embodiment, each spacer is curved at the location resting against the user (or resting on an object adjacent to the user, such as clothing). The curved edges may also serve as guides for orientation and placement of the attachment mechanism on the user. In an alternative embodiment, the standoff mechanism includes one or more projections that may be arranged in a grid. In one embodiment, the projections are rods with rounded ends. In one embodiment, the standoff mechanism is also the attachment mechanism. For instance, in one embodiment, the material on the edges of the stand-off spacers includes an adhesive. The stand-off distance prescribed by the stand-off mechanism may be between 1 and 20 millimeters. In one embodiment, the stand-off distance is between 4 and 14 millimeters. In an alternative embodiment, the stand-off distance is distinct for each transmitter and receiver.

Figure 12:
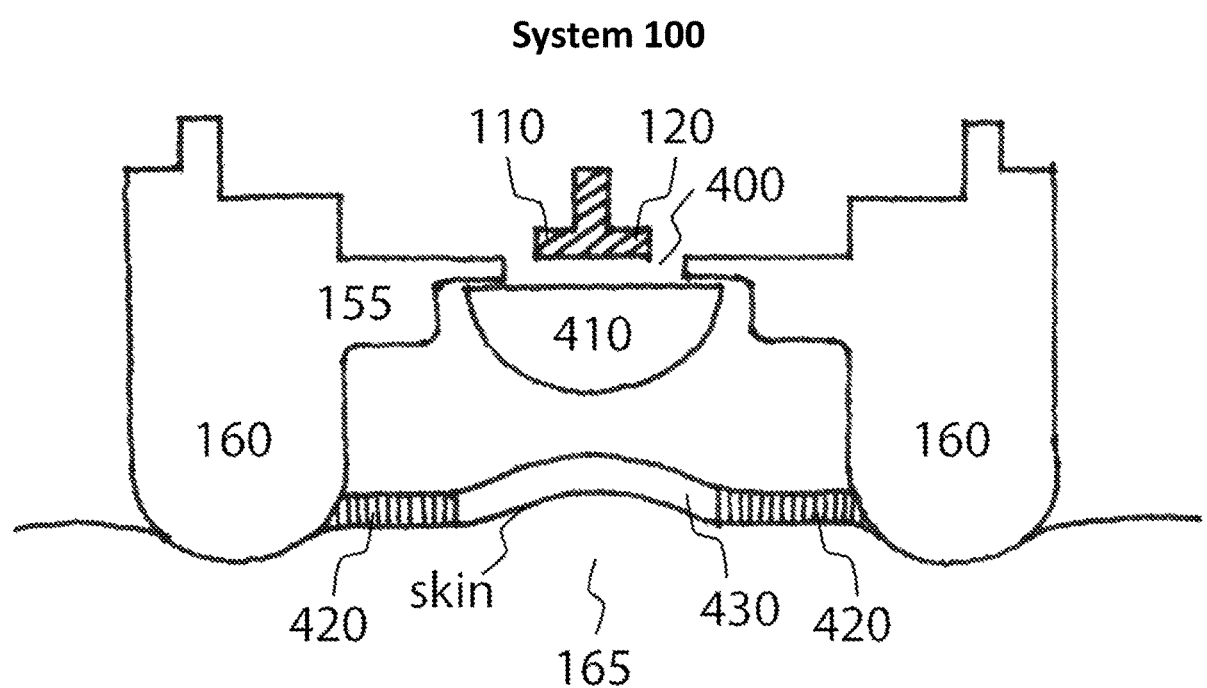
FIG. 12 is a cross-sectional view taken along the line a-b in FIG. 1.

Note that there may be material between the user's skin and the transmitter and receiver, either as part of the system 100 or separate to the system 100. In one embodiment, the region 165 between the electromagnetic transmitter and electromagnetic receiver consists of a guiding structure that enhances the received signal reflected from the target body region. With reference to FIG. 12, in one embodiment the guiding structure consists of a window 400 that is cut or inserted into the enclosure 155 and is substantially transparent to the transmit and receive signal. The window can be configured such that the reflected energy between the transmit and receive antennas and the window is less than 50%. In another embodiment, the window can be configured such that the reflected energy between the transmit and receive antennas and the window is less than 10%. The window may be constructed from low-loss materials such as air, polystyrene, polyimide or other such materials. In one embodiment, the guiding structure consists of a shaping element 410 that sits in close proximity to the transmit and receive antennas and enhances the radiation pattern of the antennas to maximize the response from the target body region. The shaping element may be constructed from low-loss insulative materials that diffract energy, metallic materials that reflect energy or absorptive materials that absorb energy. In one embodiment, the guiding structure consists of a reflective patch 430 that is placed in the target body region and utilized to increase the amount of reflection or scattering from the target. The reflective patch may be constructed from good conductors such as copper, gold, or other such materials. In one embodiment, the guiding structure consists of a mask 420 that is placed around the target body region and utilized to minimize the amount of signal acquired from regions outside of the target body region. The mask may be constructed from an absorptive or reflective material. In other embodiments, the enclosure itself 155 forms the guiding structure by choosing an appropriate shape and materials for the enclosure.

Figure 3:
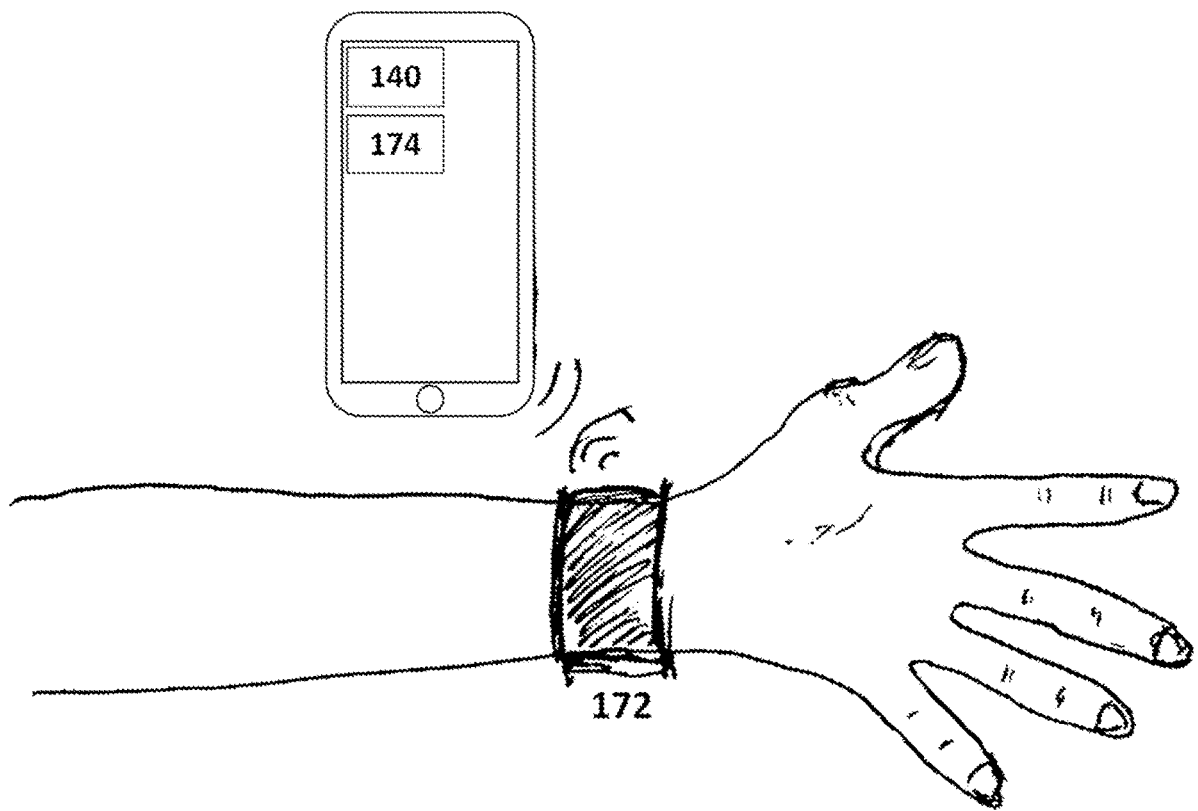
FIG. 3 is a schematic representation of further embodiment of the invention.

The activity sensor 140 functions to detect activity of the user in order to contextualize the blood pressure measurements with the user's activity state. The activity sensor is communicatively coupled to the processor 170. Examples of sensors included in the activity sensor include: inertial measurement unit, gyroscope, accelerometer, magnetometer, altimeter, optical sensor, pressure sensor, or any other suitable sensing device or combination thereof. In an alternative embodiment, the activity sensor includes a camera (e.g., visual range, multispectral, hyperspectral, IR, stereoscopic, etc.). More specifically in this alternative embodiment, the activity sensor includes a camera housed separate from the electromagnetic transmitter and electromagnetic receiver. In another embodiment, the activity sensor is contained on a separate wearable device which records motion or other data and is communicatively coupled to an external subsystem of the processor, as shown in FIG. 3. Examples of devices which can contain the activity sensor include: phone, tablet, glasses, fitness tracker, watch, medical device, healthcare monitor, or any other suitable wearable device or combination thereof.

The processor 170 can be used along with the transmitted and received signals to create a radar system. Additionally, the processor is operable between a calibration mode and an operating mode, and functions to generate the contextualized blood pressure dataset. In one embodiment of the calibration mode, measurements from the radar system and calibration sensor are utilized to create a set of calibration parameters. The calibration parameters function to correlate radar measurements to the calibration sensor, and subsequently to the derived blood pressure. In one embodiment, the processor triggers the output of signals from the electromagnetic transmitter. In one embodiment, the calibration sensor consists of a second electromagnetic transmitter and electromagnetic receiver in communication with the processor, thus forming a duality of radar systems. The processor receives signals from the first and second radar systems and measures motion such as arterial pulsing in two locations along the artery. Time delay between the pulse signals is collected at the first and second radar systems; the time delay functions to calculate an arterial pulse wave velocity, which functions in turn to derive blood pressure or a proxy for blood pressure. Alternatively or additionally, the processor is configured to calculate the pulse transit time from the pulse signal datasets. In another alternative, the processor analyzes the waveform shape to derive blood pressure, including: pulse waveform analysis, frequency analysis, amplitude analysis, filtering, or any other suitable form of signal analysis or combination thereof. More specifically, the processor in calibration mode may identify a start time of an arterial pulse waveform recorded in the pulse signal datasets. Even more specifically, this start time may be determined with the aid of one or more template arterial pulse waveform shapes. Alternatively, this start time may be determined through any suitable method of waveform analysis, including: frequency analysis, amplitude analysis, or filtering or combination thereof. In another embodiment, the calibration sensor consists of a second electromagnetic receiver that receives energy from the first transmitter to form the second radar system.

In one embodiment of the operating mode, the processor is used with the transmitted and received signals to create a radar system and is additionally coupled to the activity sensor. In this embodiment, the processor is configured to use measurements from the radar system as well as the activity sensor, and is configured to generate a contextualized blood pressure dataset based on the radar data and the set of calibration parameters. In one embodiment the calibration sensor can be turned off subsequent to the calibration parameter generation, while the processor continues to periodically generate radar data from the radar system. In an alternative embodiment, the calibration sensor continues to function, and both the radar system and calibration sensor are used to periodically determine blood pressure. In one embodiment, the blood pressure dataset is generated by categorizing the received activity sensor data into activity state categories, and subsequently labeling the blood pressure based on the categorization. In one embodiment, one of the categories indicates that the user has been at a low level of activity for a given period of time (i.e. 'at rest'). In one embodiment, the period of time is greater than 1 minute. In one embodiment, the period of time is greater than 5 minutes. Additionally, in one embodiment, the processor transitions to calibration mode when the activity sensor data is categorized as 'at rest.' Alternatively, the processor records data from the radar system and calibration sensor only when the activity sensor data is categorized as 'at rest.'

The processor can include a local microprocessor subsystem coupled to the attachment mechanism 150 or the housing 155 within the attachment mechanism. Alternatively, the processor includes a local processing subsystem 172 as well as a remote processing subsystem 174, as shown in FIG. 3. Both subsystems can include a communication system, which are communicatively coupled to one another. In one embodiment, this remote processing subsystem is housed on a phone, tablet, computer, or any other suitable device with processing capabilities or combination thereof. In another alternative, the processor includes a local communication system coupled to the attachment mechanism and a remote processing subsystem (including a communication system) housed separately. The communication system in any embodiment can include one or more radios or any other suitable component. The communication system can be a long-range communication system, a short-range communication system, or any other suitable communication system. The communication system can facilitate wired and/or wireless communication. Examples of the communication system include: 802.11x, Wi-Fi, Wi-Max, WLAN, NFC, RFID, Bluetooth, Bluetooth Low Energy, BLE long range, ZigBee, cellular telecommunications (e.g., 2G, 3G, 4G, LTE, etc.), radio (RF), microwave, IR, audio, optical, wired connection (e.g., USB), or any other suitable communication device or combination thereof.

The processor may optionally be communicatively coupled to additional sensors, including: electrocardiography sensor, heart rate monitor, photoplethysmography sensor, temperature sensor, blood pressure meter, laser sensor, or any other suitable sensor or combination thereof.

The processor can be powered by a power supply. The power supply can be a wired connection, wireless connection (e.g., inductive charger, RFID charging, etc.), a battery (e.g., secondary or rechargeable battery, primary battery, etc.), energy harvesting system (e.g., solar cells, piezoelectric systems, pyroelectrics, thermoelectrics, etc.), or any other suitable system or combination thereof.

Figure 5:
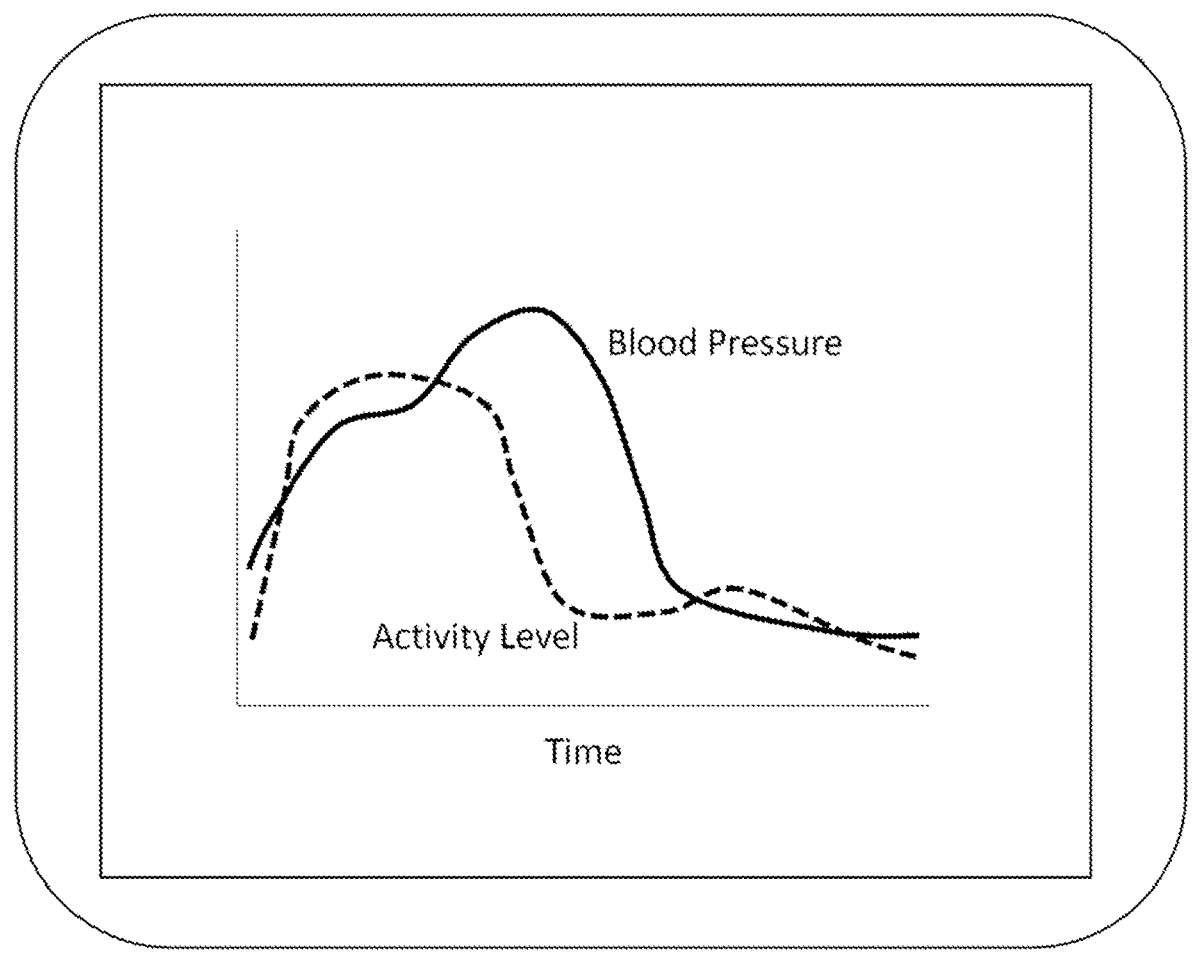
FIG. 5 is a schematic representation of another embodiment of the invention.

As shown in FIG. 4, in one embodiment, a display 175 is optionally included in the system to display the contextualized blood pressure dataset. The display can be configured to label blood pressure measurements in accordance with the corresponding detected activity state. In another variation (as shown in FIG. 5), the display plots the blood pressure and the activity state. In another variation, the display displays only blood pressure measurements taken during certain activity states. In this variation, the display can display only blood pressure measurements taken when the activity state was categorized as 'at rest.' In one embodiment, the display module is an application on a phone, tablet, or computer. Alternatively, the display is fixed to the attachment mechanism or standoff mechanism.

2. A Method for Generating a Contextualized Blood Pressure Dataset

Figure 6:
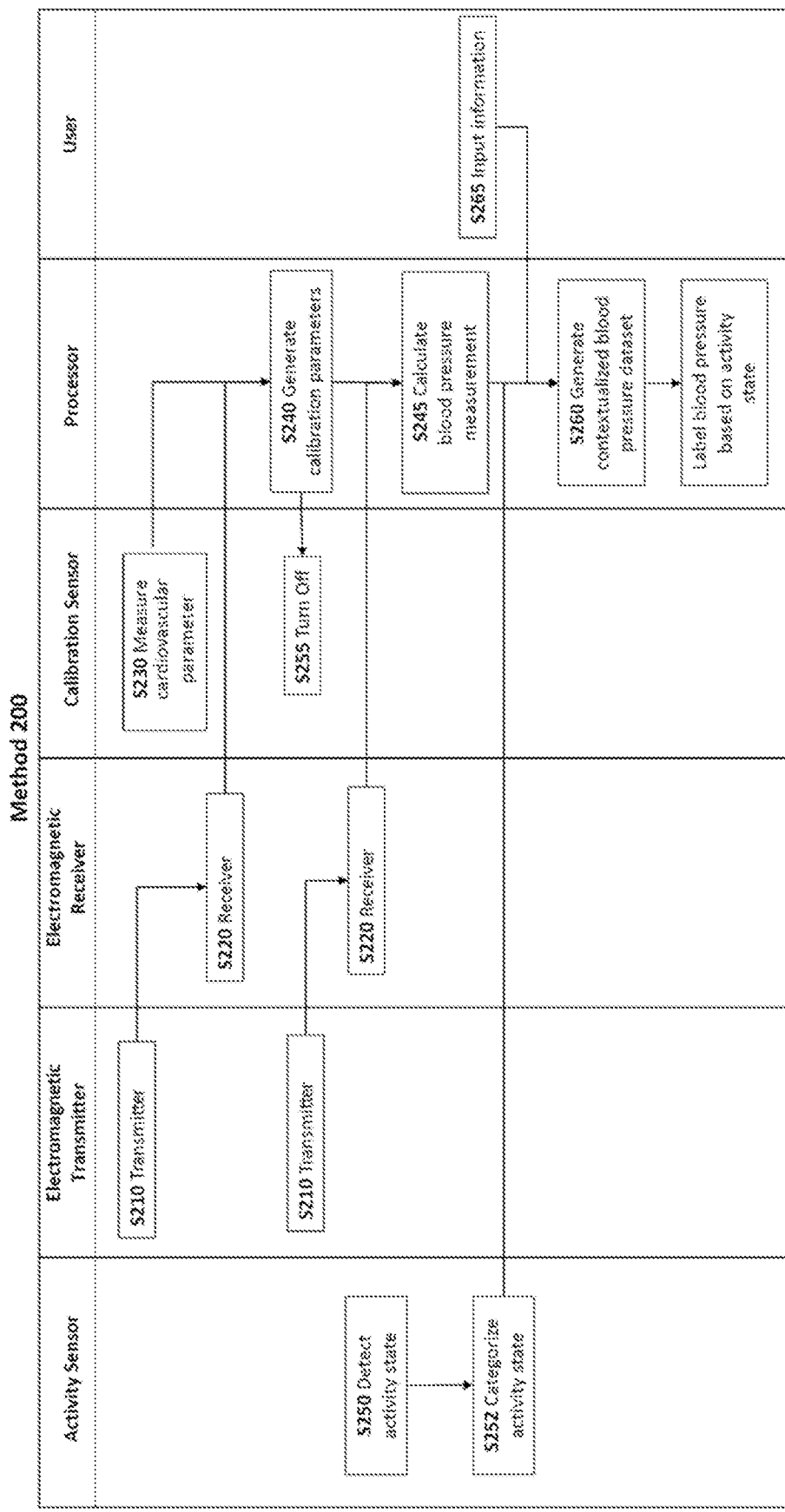
FIG. 6 is a flowchart representation of an alternative embodiment of the invention.
Figure 7:
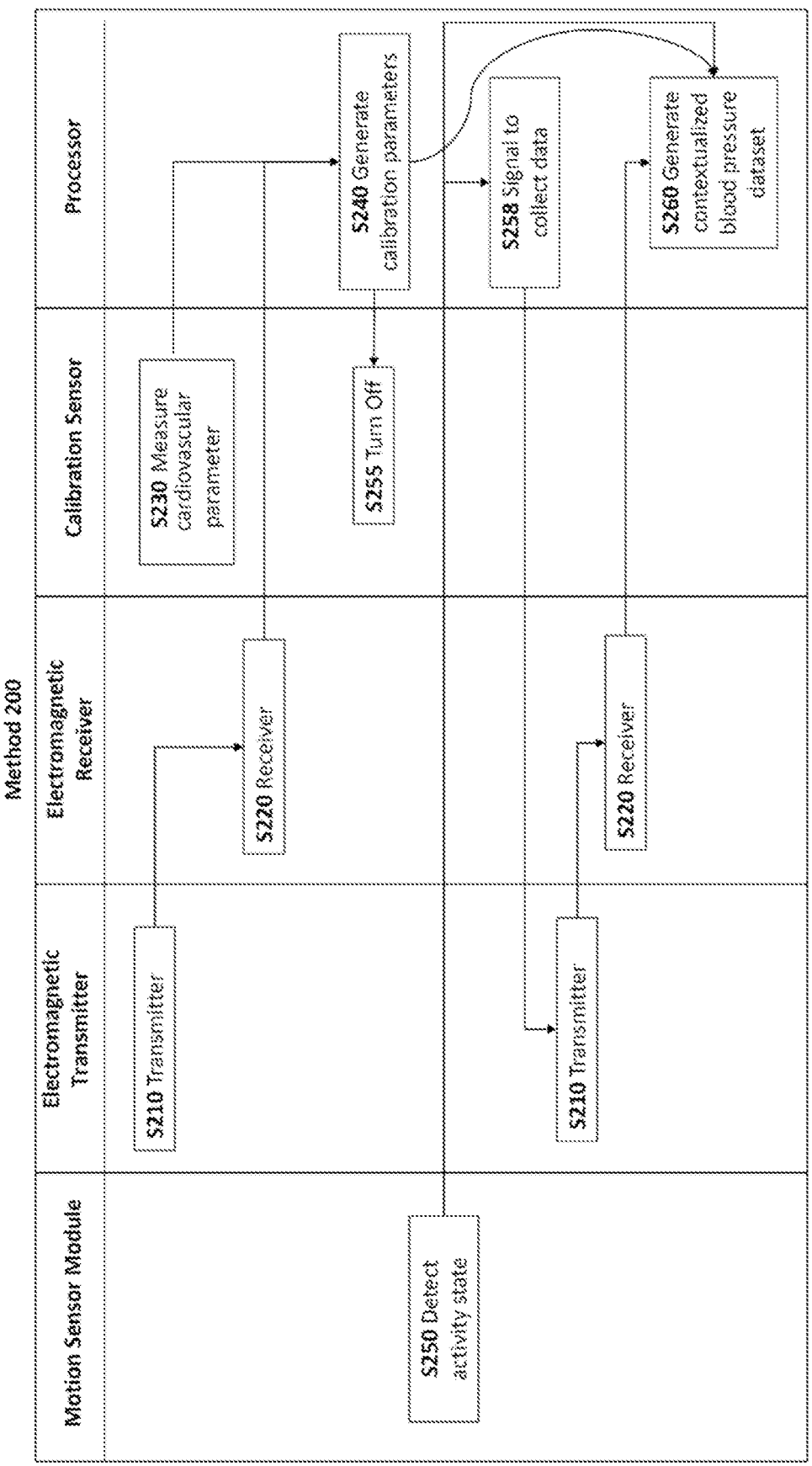
FIG. 7 is a flowchart representation of another embodiment of the invention.

As shown in FIG. 6, a method 200 for generating a contextualized blood pressure dataset for a user preferably includes transmitting a set of electromagnetic signals directed towards an artery of the user via an electromagnetic transmitter S210 and collecting, at an electromagnetic receiver, a received reflected signal dataset that includes the signals transmitted by the electromagnetic transmitter S220. The method additionally includes measuring the cardiovascular parameters of a user with a calibration sensor S230 and generating a set of calibration parameters that correlate the reflected signal dataset of the receiver to the measured cardiovascular parameters S240. The method also includes detecting an activity state of the user with an activity sensor S250 and generating a contextualized blood pressure dataset with the user's blood pressure linked to the activity state S260. The method 200 functions to periodically determine the user's blood pressure non-invasively and to provide context for the blood pressure readings. The method 200 may additionally or alternatively include a step collecting blood pressure data at selected times based on the detected activity state of the user (as shown in FIG. 7); this step can be used to provide a more accurate blood pressure dataset. The method 200 is preferably implemented by the system 100, but may additionally or alternatively be implemented by any system capable of interfacing with a receiver.

The step transmitting a set of signals directed towards a target body region such as an artery of the user via an electromagnetic transmitter S210 preferably functions to transmit signals that reflect off of the skin of the user and are then received in step S220. In an alternative embodiment, the received signals are enhanced via guiding structures such as a window or shaping element to maximize transmission of energy between the transmit and receive antennas and the target. In another alternative embodiment, the guiding structure consists of a reflective patch fixed to the skin of the user, where the material moves in correlation with movement of the artery. In this case, the material thickness can be less than 2 mm; or less than 1 mm. In another alternative embodiment, the guiding structure consists of a mask fixed to the skin of the user, where the material leaves an exposed target body region such as an artery of the user and absorbs energy that strikes other regions.

The preferred embodiment of S210 includes transmitting millimeter-wave signals. More preferably, the electromagnetic transmitter transmits signals with a frequency of 30 to 300 GHz. In another variation, the transmitted signals have a frequency between 57 and 63 GHz. In one embodiment, S210 includes transmitting frequency modulated continuous wave signals that can be used for frequency modulated continuous wave radar. In another embodiment, S210 includes transmitting continuous wave signals. In another embodiment, S210 includes transmitting pulsed signals.

The step collecting a reflected signal dataset S220 functions to receive signals generated by the electromagnetic transmitter and reflected off of the user. The timing, shape, phase and amplitude of the received signal will be affected by the arterial pulse waveform, which will in turn enable the determination of the user's blood pressure. In one embodiment, S220 includes collecting frequency modulated continuous wave signals. In another embodiment, S220 includes collecting continuous wave signals. In another embodiment, S220 includes collecting pulsed signals. Preferably, S220 includes a sub-step: mixing, filtering and performing radar signal processing on the reflected signal dataset to extract information related to the position and motion of the target body region of the user such as the arterial pulse waveform. S220 can include sampling the reflected signal dataset. Alternatively, mixing, filtering and signal-processing of the reflected signal dataset may occur during S240 or with any other suitable step.

The step measuring the blood pressure of a user with a calibration sensor S230, preferably functions to enable the calculation of calibration parameters for the receiver such that received data from the receiver can be used to derive blood pressure without the use of the calibration sensor. Alternatively, the calibration sensor is used periodically to prevent loss of accuracy in the calibration over time. In another alternative, the calibration sensor is employed when the detected activity state changes, the temperature changes, or based on any other relevant signal. The calibration sensor is preferably a second receiver. Alternately, the calibration sensor is a second transmitter and second receiver. More preferably, the calibration procedure is the method substantially described as method 300. However, the calibration sensor may alternatively be a blood pressure meter, a photoplethysmogram sensor, an optical sensor, or any other suitable blood pressure measurement device or combination thereof. Even more preferably, S230 includes turning off the calibration sensor subsequent to calibration. Alternatively, S230 may include electrically or communicatively coupling the calibration sensor to a processor which, in turn, is electrically coupled to the receiver. More specifically, S230 may include uncoupling the calibration sensor subsequent to calibration.

The step generating calibration parameters that correlate the reflected signal dataset of the receiver to the measured blood pressure S240 functions to enable the derivation of blood pressure without the use of the calibration sensor. In this embodiment, S240 is followed by a repetition of steps S210 and S220. The calibration parameters are then used in another step S245: calculating the blood pressure from the reflected signal dataset collected during the repeated step S220. In the preferred embodiment, S245 is performed without the use of the calibration sensor. However, alternatively, S240 functions to increase the accuracy of the blood pressure readings by enabling an analysis of any shifts in the reflected signal dataset relative to the blood pressure correlation. In this embodiment, the calibration sensor continues to periodically be used and the calibration parameters are re-calculated. Preferably, changes in the calibration parameters are tracked with reference to the detected activity state. More preferably, shifts in the calibration parameters are additionally or alternatively tracked with reference to alternate sensor data or user input.

Calibration parameters are preferably parameters modifying one or more equations that translate the reflected signal dataset to a blood pressure value. The variables of the reflected signal dataset which are preferably used as inputs in equations include: amplitude, frequency, Fast Fourier transform analysis results, shape, width, derivative, or any other suitable aspect of the waveform or any combination thereof. Alternatively, the calibration parameters are the equations that translate the reflected signal dataset to a blood pressure value. The blood pressure value is preferably two numbers: one corresponding to systolic blood pressure and one corresponding to diastolic. Alternatively, the blood pressure value is a single number representing a combination of systolic and diastolic pressure—including total systolic or total diastolic pressure. In another alternative, the blood pressure value is one or more proxy values that correlate or correspond to a relevant blood pressure measurement. In another alternative, the blood pressure value corresponds to a category of blood pressure. Example categories of blood pressure include: high, low, somewhat high, somewhat low, unsafe, and normal.

Figure 8:
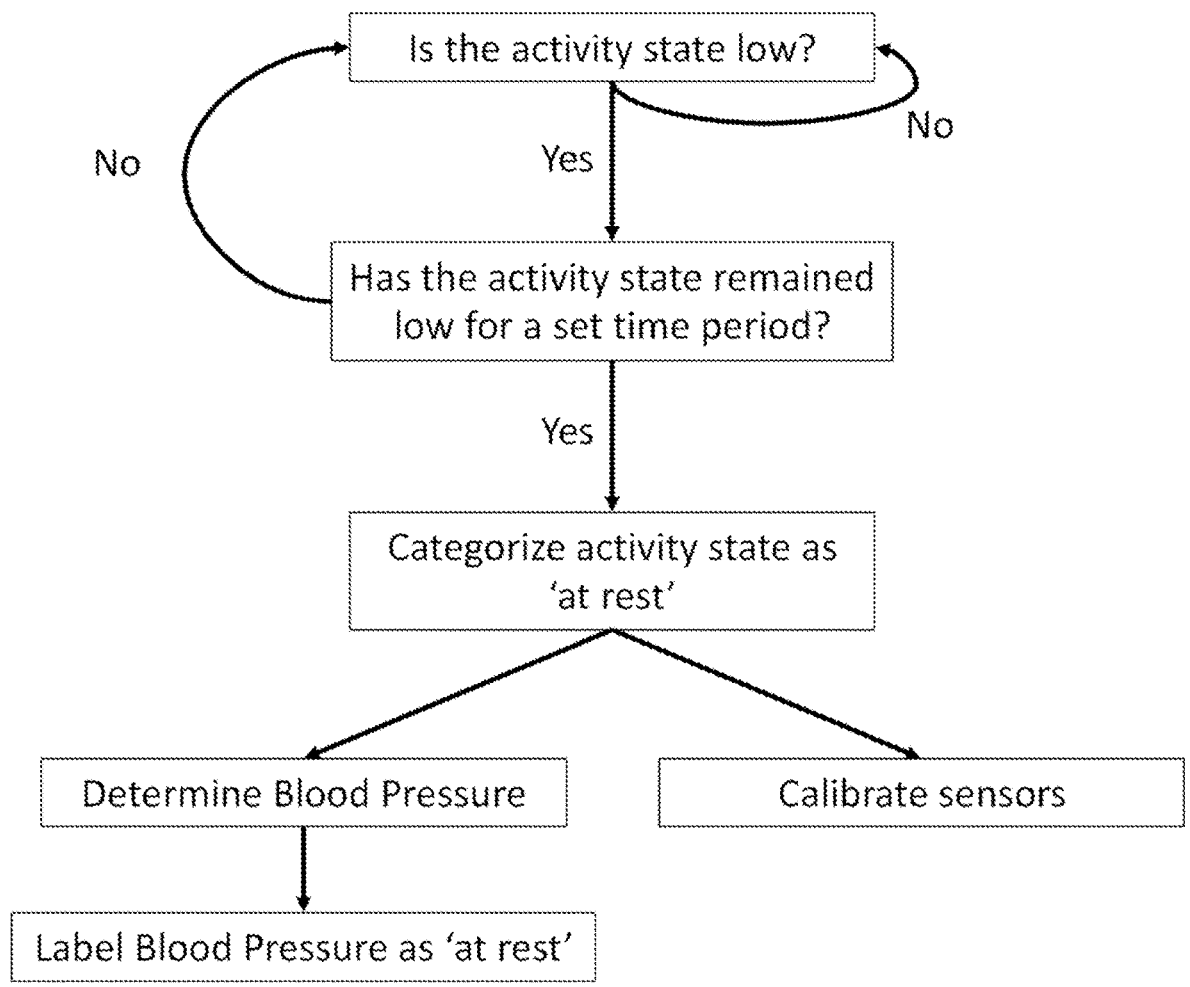
FIG. 8 is a flowchart representation of a further embodiment of the invention.

The step detecting an activity state of the user with an activity sensor S250 preferably functions to provide context for the blood pressure measurements. More preferably, the activity state is categorized based on threshold values for levels of motion. Even more preferably, any detected activity state corresponds to at least one activity state category. Some example categories of user activity states include: inactive, active, resting, walking, running, and sleeping. Most preferably, activity states are determined using thresholds for activity levels as well as thresholds for time during which the motion remains substantially above or below a given an activity threshold value for a given time duration threshold. For example, as shown in FIG. 8, one of the activity state categories indicates that the user has been at a low level of activity for a given period of time (i.e. 'at rest'). Even more preferably, the period of time is greater than 1 minute. Most preferably, the period of time is greater than 5 minutes. Examples of activity detection methods include the use of: inertial measurement unit, gyroscope, accelerometer, magnetometer, altimeter, optical sensor, pressure sensor, or any other suitable communication module or combination thereof. In another embodiment, S250 includes electrically or communicatively coupling the activity sensor to a processor which, in turn, is electrically coupled to the receiver.

In an alternative embodiment of the method 200, S250 functions to enable the regulation of the timing of blood pressure measurements. As an example of such an embodiment, as shown in FIG. 7, the following step is included: S258 triggering the generation of a blood pressure dataset based on the detected activity state. Preferably, S210, S220, S230, and S240 were performed prior to S258; in this variation, the receiver has already been calibrated with reference to a measured blood pressure, so the steps following S258 would be S210 (again) and S220 (again). More preferably, S258 is performed when the activity state is below or above a certain motion threshold value. Even more preferably, S258 is performed when the activity state is below (or above) a certain motion threshold value and remains substantially below (or above) that threshold value for a specified period of time (as shown in FIG. 8). Most preferably, that period of time is greater than 5 min. The period of time can alternatively be any suitable time period, and the motion threshold value can be any threshold suitable for categorizing the received activity sensor signals. Note that if the activity state briefly crosses the threshold (i.e. less than 5 seconds), the state may still be considered below (or above) the threshold for the specified period of time. In an alternative embodiment, the receiver is continually collecting reflected signal datasets, and it is the generation of the contextualized blood pressure dataset that is triggered based on the activity state. Note that, in one embodiment, the contextualized blood pressure dataset is a blood pressure dataset where the blood pressure measurements were taken during a specific category of the detected activity state. For example, the contextualized blood pressure dataset contains blood pressures taken when the detected motion of the user was categorized as 'at rest.'

In another alternative embodiment of the method 200, S250 functions to enable the regulation of the timing of sensor calibration. Preferably, this embodiment would include the following step: triggering the generation of calibration parameters that correlate the reflected signal dataset of the receiver to the measured blood pressure. More preferably, S210, S220, and S230 are periodically performed, while S240 is performed based on the detected activity state. More preferably, the triggering of S240 is performed when the activity state is below or above a certain motion threshold value. Even more preferably, the triggering of S240 is performed when the activity state is below (or above) a certain motion threshold value and remains substantially below (or above) that threshold value for a specified period of time (as shown in FIG. 8 and as previously described). Most preferably, that period of time is greater than 5 min. The period of time can alternatively be any suitable time period, and the motion threshold value can be any threshold suitable for categorizing the received activity sensor signals. In another alternative, the embodiment could similarly include triggering other steps including: S210, S220, and S230.

The step generating a contextualized blood pressure dataset with the user's blood pressure linked to the activity state S260 preferably functions to combine the data received from the receivers with the detected activity state, thus providing users and medical professionals with an increased understanding of a user's cardiovascular health. More preferably, S260 includes labeling the blood pressure based on an activity state category corresponding to the detected activity state. Embodiments of the activity state categorization substep are detailed in S240. Alternatively, the activity state categorization substep occurs during S260. Most preferably, the blood pressure is also labeled with a time corresponding to the time the blood pressure reading or activity state reading was taken.

In an alternative embodiment, S260 functions to clarify a blood pressure dataset by grouping or filtering the blood pressure data based on the user's activity state. Preferably in this embodiment, S250 was performed for each relevant blood pressure reading, thus enabling each reading to correspond to an activity state. In this embodiment, S260 then groups the blood pressure readings based on the corresponding activity state to generate a contextualized blood pressure dataset. More preferably, there is a group corresponding to a rest state where the activity state was detected as a low level of activity for a given period of time (as shown in FIG. 8). Most preferably, the contextualized blood pressure dataset is filtered with preference to the group corresponding to a rest state. Alternatively, there are multiple groups given preference in the filtering of the contextualized dataset substep.

In another embodiment of method 200, there is a step: collecting additional data from a sensor. This step functions to provide additional contextual information to the blood pressure dataset. Sensors can include: cameras (e.g., visual range, multispectral, hyperspectral, IR, stereoscopic, etc.), orientation sensors (e.g., accelerometers, gyroscopes, altimeters), acoustic sensors (e.g., microphones), optical sensors (e.g., photodiodes, etc.), temperature sensors, pressure sensors, flow sensors, vibration sensors, proximity sensors, chemical sensors, electromagnetic sensors, force sensors, electrocardiography sensors, heart rate monitors, photoplethysmography sensors, blood pressure meters, or any other suitable sensor. In this embodiment, S260 combines blood pressure, detected activity state, and the additional sensor data to generate a contextualized blood pressure dataset.

In another embodiment of method 200, as shown in FIG. 6, there is an additional step: inputting a user-defined information S265. This additional step functions to enable users (or medical practitioners) to provide additional context, relating to the user's: cardiovascular parameters, age, gender, race, medical history, health, fitness, general activity level, current activity state, activity state at a certain time, or any other relevant contextual information. In this embodiment, S260 combines blood pressure, detected activity state, and the user input, or any combination thereof, to generate a contextualized blood pressure dataset. More preferably, there is an additional step of combining blood pressure datasets from multiple users into a conglomerate dataset and grouping the conglomerate dataset by factors inputted in S265. This conglomerate dataset enables the analysis of blood pressure data for larger populations. Most preferably, this conglomerate dataset generation includes a substep of attaining consent from the users. Alternatively, the user-defined information is used to prescribe thresholds for activity state categories. Another alternative uses the user-defined information to prescribe thresholds for blood pressure categories. In another embodiment, S265 enables users to correct erroneous activity sensor readings. Preferably, preference is given to the user-defined activity state over the activity sensor detected activity state in the contextualized blood pressure dataset. Alternatively, preference is given to the activity sensor-detected activity state.

As shown in FIGS. 4 and 5, in one embodiment, an additional step is included: displaying the contextualized blood pressure dataset. In the case of system 100, this step is performed with a display module 175. This step preferably functions to display blood pressure over a period of time in the context of the activity state in which the blood pressure was determined. Preferably, the step includes labeling on the display blood pressure measurements in accordance with the corresponding detected activity state (as shown in FIG. 4). In another variation (as shown in FIG. 5), the step includes plotting blood pressure and the activity state over a period of time. Alternatively, this step functions to display the blood pressure readings which are considered relevant based on the activity state in which the blood pressure was determined. More preferably in this variation, the display module displays blood pressure measurements taken when the activity state was categorized as 'at rest.' This displaying step can also function to illustrate areas of concern to the user or physician. For example, in one embodiment, the display module shows a plot of blood pressure and activity level over the course of a period of time (FIG. 5); a time were the blood pressure is higher than expected relative to the activity state could indicate that the user was stressed at that time.

Figure 9:
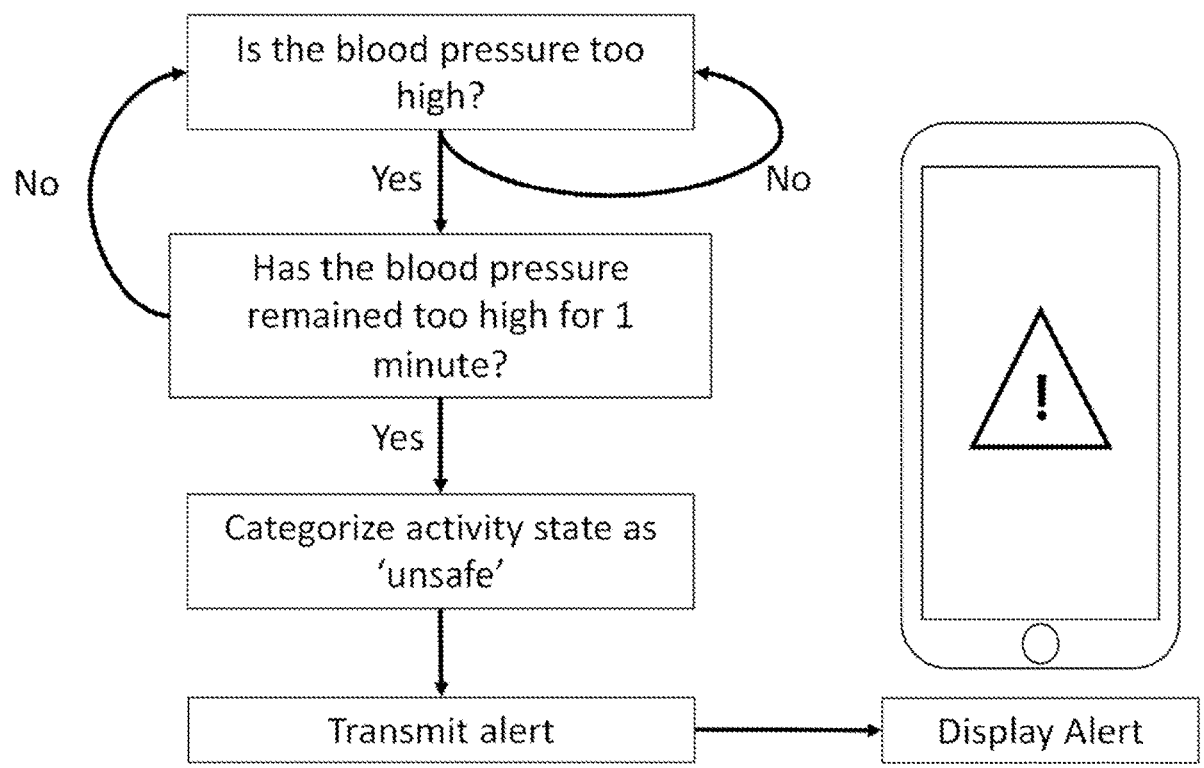
FIG. 9 is a flowchart representation of a further embodiment of the invention.

As shown in FIG. 9, in one embodiment of method 200, the following additional steps are included: setting a blood pressure threshold such that when the blood pressure is above the blood pressure threshold, the blood pressure corresponds to an unsafe state, and transmitting an alert if the blood pressure is beyond the blood pressure threshold. Preferably, the unsafe state corresponds to systolic blood pressure above 120 mmHg or below 90 mmHg, and diastolic blood pressure above 80 mmHg or below 60 mmHg. Alternatively, the unsafe state threshold is any suitable blood pressure value, including: systolic blood pressure, diastolic blood pressure, and average blood pressure. The unsafe state may depend on the race, gender, age, medical history, or any other relevant factor. Even more preferably, multiple levels of unsafe states are prescribed, including a warning state when systolic pressure is above 120 mmHg, but below 140 mmHg. Alternatively, the unsafe state is prescribed by the user, a physician, or any other suitable person. In another embodiment, the unsafe state is determined specifically for each user. For example, the blood pressure is first measured at an initial time, and this initial blood pressure determines the thresholds for unsafe state. More preferably, the initial blood pressure is measured during one or more activity states and the unsafe state depends on the detected activity state. The method may additionally include displaying an alert if the alert is transmitted. For example, in the case of a patient with high blood pressure, if the measured blood pressure (systolic or diastolic blood pressure) is higher than a safe value, and remains high for at least 5 minutes, an alert is transmitted to the user's physician as well as displayed on the user's phone.

3. A Method for Calibrating Receivers to Derive Blood Pressure

Figure 10:
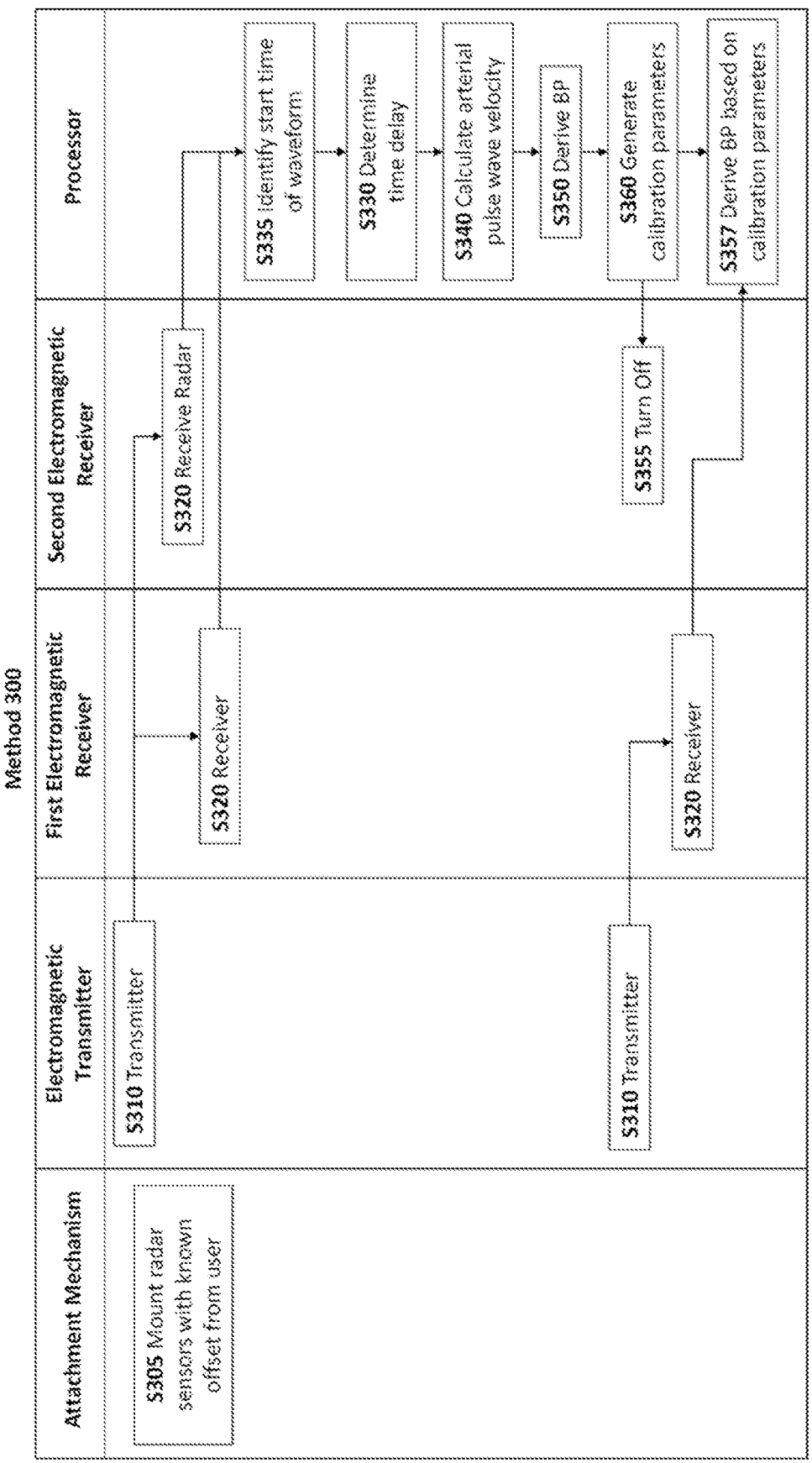
FIG. 10 is a flowchart representation of an alternative embodiment of the invention.

As shown in FIG. 10, a method 300 for calibrating receivers to derive blood pressure of a user includes: transmitting a set of signals directed towards an artery of the user via an electromagnetic transmitter S310; collecting, at both a first electromagnetic receiver and a second electromagnetic receiver, a first reflected signal dataset and a second reflected signal dataset which includes the signals transmitted by the transmitter S320; determining a time delay between the reflected signal datasets collected at the first and second receivers S330; calculating an arterial pulse wave velocity based on the time delay S340; deriving blood pressure of the user based on the arterial pulse wave velocity S350; and generating calibration parameters that substantially correlate the reflected signal dataset of the first receiver to the blood pressure S360. The method 300 functions to calibrate a first receiver via a second receiver, thus allowing the non-invasive derivation of blood pressure from the first receiver. The method 300 may additionally or alternatively include collecting activity sensor data, which can be used to provide a context for the blood pressure readings.

The preferred embodiment of method 300 includes a system as described by system 100. A further or alternative embodiment of method 300 includes any step of method 200 or any combination thereof.

The step transmitting a set of signals directed towards an artery of the user via an electromagnetic transmitter S310 preferably functions to generate signals that reflect off of the skin of the user and are then received in step S320. Preferably, the signals are transmitted by two transmitters, each mounted with reference to one of the first and second electromagnetic receivers, thus enabling increased precision in the reflected signal datasets collected in S320. In another embodiment, S310 is performed by one electromagnetic transmitter. More preferably in this embodiment, S310 includes transmitting a set of signals at a non-zero angle relative to the line representing the shortest distance from the transmitter to the artery of interest. Step S310 is similar to step S210; additional variations of S310 are detailed in the discussion of embodiments of S210.

The step collecting, at both a first and a second electromagnetic receiver, a reflected signal dataset S320 preferably functions to receive signals generated by the electromagnetic transmitter and reflected off of the user. The timing, shape, phase and amplitude of the received signals will be affected the arterial pulse waveform, which will in turn enable the determination of the user's blood pressure. In the preferred embodiment, S320 includes collecting frequency modulated continuous wave signals. In another embodiment, S320 includes collecting continuous wave signals. In another embodiment, S320 includes collecting pulsed signals. Preferably, S320 includes a sub-step: mixing, filtering and performing radar signal processing on the first and second reflected signal datasets to extract information related to the position and motion of the target body region of the user such as the arterial pulse waveform. S320 can include sampling the reflected signal datasets. Alternatively, mixing, filtering and signal-processing of the reflected signal datasets may occur during S330 or with any other step.

Figure 11:
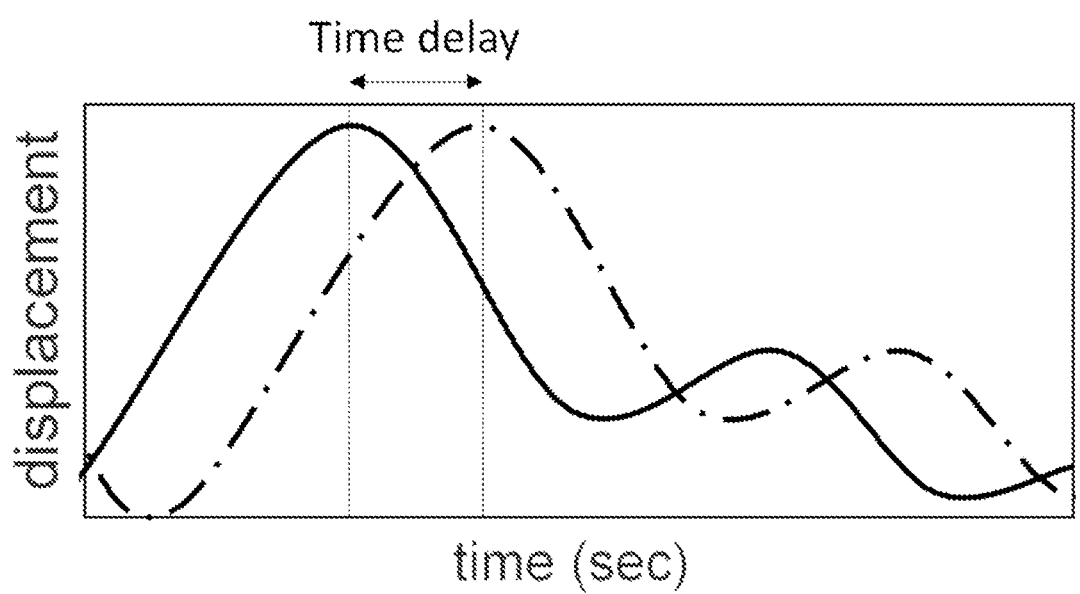
FIG. 11 is a representative graph of another embodiment of the invention.

As shown in FIG. 11, The step determining a time delay between the reflected signal datasets collected at the first and second receivers S330 preferably functions to enable the calculation of an arterial pulse wave velocity, which in turn can be used to derive blood pressure or a proxy for blood pressure. More preferably, the time difference represents the time for an arterial pulse wave to travel a distance along the artery corresponding to a receiver spacing distance separating the first and second receivers. However, the time delay may include an additional delay (positive or negative) due to the angles at which the signals are transmitted and received. For example, if the distance separating the first receiver from the transmitter (or the portion of the transmitter transmitting signals for the first receiver) is different than the distance separating the second receiver from the transmitter (or the portion of the transmitter transmitting signals for the second receiver), then the time delay between the first and second reflected signal datasets may differ from the pulse transit time of the arterial pulse along a distance equivalent to the sensor spacing distance. Similarly, if the angle at which the first receiver receives reflected signals is different than the angle for the second receiver, the time delay may not be representative of the pulse transit time along a distance equivalent to the sensor spacing distance. In such cases, step S340 will preferably account for the differences.

In the preferred embodiment, S330 includes identifying a start time of an arterial pulse waveform recorded in the reflected signal datasets. Even more preferably, this start time is determined with the aid of one or more template arterial pulse waveform shapes. Alternatively, this start time may be determined through any suitable method of waveform analysis, including: frequency analysis, amplitude analysis, or filtering or combination thereof. The start time is defined as any point along the waveform, including: a peak, valley, rising waveform, falling waveform or any suitable location in the reflected signal datasets. Alternatively, the start time may shift depending on the shape of waveform being analyzed. More preferably, when the start time location determination method changes for differing reflected signal datasets, the start time continues to represent equivalent positions in the first and second reflected signal datasets, such that the difference between the start times corresponds to the time delay of the arterial pulse.

The step calculating an arterial pulse wave velocity based on the time delay S340 preferably functions to enable the derivation of blood pressure. In the preferred embodiment, the time delay represents the pulse transit time for an arterial pulse along a distance equivalent to the sensor spacing distance. Thus, in this embodiment, S340 includes dividing the sensor spacing distance by the time delay. Alternatively, the pulse transit time is first calculated from the time delay. More specifically, calculating the pulse transit time from the time delay includes an adjustment for the distance and angle that the signals travel from the transmitter to the first and second receiver. For example, if signals travel further from the transmitter to the second receiver (after reflecting) when compared to the distance radar signals travel from the transmitter to the first receiver (after reflecting), then the time delay may include an additional delay (positive or negative) compared to the pulse transit time. Preferably, this additional delay is calculated based on the relative locations of the receivers and transmitter. More preferably, this additional delay is subtracted from the time delay to calculate pulse transit time, which in turn is used to calculate arterial pulse wave velocity. Alternatively, this additional delay is used during S350.

The step deriving blood pressure of the user based on the arterial pulse wave velocity S350 preferably functions to translate the calculated arterial pulse wave velocity into a blood pressure value. Pulse wave velocity has been shown to correlate with blood pressure. Preferably, S350 includes the use of a correlation between pulse wave velocity and blood pressure derived from one or more subjects. Alternatively, an additional sensor is used to calibrate pulse wave velocity to blood pressure for the user. Some examples of additional sensors include: a blood pressure meter, a photoplethysmogram sensor, an optical sensor, or any other suitable blood pressure measurement device or combination thereof. In another embodiment, S350 is additionally or alternatively performed through analysis of the waveform shape of the reflected signal dataset to derive blood pressure, including: pulse waveform analysis, frequency analysis, amplitude analysis, filtering, or any other suitable form of signal analysis or combination thereof.

The blood pressure value is preferably two numbers: one corresponding to systolic blood pressure and one corresponding to diastolic. Alternatively, the blood pressure value is a single number representing some combination of systolic and diastolic pressure—including total systolic or total diastolic pressure. In another alternative, the blood pressure value is one or more proxy values that correlate or correspond to a relevant blood pressure measurement. In another alternative, the blood pressure value corresponds to a category of blood pressure. Example categories of blood pressure include: high, low, somewhat high, somewhat low, unsafe, and normal.

The step generating calibration parameters that substantially correlate the reflected signal dataset of the first receiver to the blood pressure S360 preferably functions to enable the derivation of blood pressure measurements for the user. In this embodiment, S360 is followed by a repetition of steps S310 and S320. The calibration parameters are then used in S357: calculating the blood pressure from the reflected signal dataset collected during the repeated step S320. In the preferred embodiment, S357 is performed without the use of the second receiver. More preferably, S360 includes turning off the second receiver subsequent to calibration. Alternatively, S360 functions to increase the accuracy of the blood pressure readings by enabling an analysis of any shifts in the reflected signal dataset relative to the blood pressure correlation. In this embodiment, the second receiver continues to periodically collect data and the calibration parameters are re-calculated. Preferably, changes in the calibration parameters are tracked with reference to alternate sensor data or user input data.

Calibration parameters are preferably parameters modifying one or more equations that translate the reflected signal dataset to a blood pressure value. The variables of the reflected signal dataset which are preferably used as inputs in the equations include: amplitude, frequency, Fast Fourier transform analysis results, shape, width, derivative, or any other suitable aspect of the waveform or any combination thereof. Alternatively, the calibration parameters are equations that translate the reflected signal dataset to a blood pressure value.

Method 300 may additionally include a step S305: mounting the first and second electromagnetic transmitters and first and second electromagnetic receivers to the user at a known stand-off distance. S305 functions to fix the first and second transmitters and receivers to the user as well as to offset the first and second transmitters and receivers at a known stand-off distance from a point of interest on the user. This stand-off enables the user's skin overlaying the artery to move relative to the transmitters and receivers; it also enables the target body region to be maintained outside of the reactive near-field of the electromagnetic transmitters and receivers—thus preventing unpredictable performance. In the preferred embodiment, the stand-off distance prescribed by the stand-off mechanism is between 1 and 20 millimeters. Even more preferably, the stand-off distance is between 4 and 14 millimeters. In an alternative embodiment, the stand-off distance is distinct for each transmitter and receiver.

In one embodiment, S305 additionally functions to fix the first and second electromagnetic receivers at a known spacing distance apart. preferably, the spacing distance is greater than 0.25 centimeters. Even more preferably, the spacing distance is greater than 1 centimeter.

In one embodiment, S305 includes mounting the first and second receivers to the user with a wristband. Alternatively, S305 includes the use of: Velcro, straps, adhesive, and/or silicone. In a preferred embodiment, S305 includes mounting to a separate device which is mounted to the user. More preferably, S305 includes mounting the electromagnetic transmitters and electromagnetic receivers to a wearable fitness device. Alternatively, S305 includes mounting to an exercise machine and enabling temporary mounting to a user.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

The invention claimed is:

1. A wearable system for measuring an arterial pulse waveform of a user, the system comprising:
   a radio frequency (RF) electromagnetic transmitter for transmitting an RF signal having a frequency in the range of 30 GHz to 300 GHz towards a target body region on the user, said target body region being skin over an artery of the user;
   a radio frequency (RF) electromagnetic receiver for receiving reflected RF signals from the target body region;
   an attachment mechanism that is adaptable to position the RF electromagnetic transmitter and the RF electromagnetic receiver proximal to the target body region and to maintain the position of the RF electromagnetic transmitter and the position of the RF electromagnetic receiver relative to the target body region; and
   a stand-off mechanism for positioning on the user an antenna for the RF electromagnetic transmitter and an antenna for the RF electromagnetic receiver such that a standoff distance from the user's skin is within a range of between 1 mm and 20 mm for each of the RF electromagnetic transmitter and the RF electromagnetic receiver, wherein the standoff mechanism is configured to substantially avoid perturbing the physiology of the target body region and enable the user's skin and tissues overlying the artery to move freely with respect to the RF electromagnetic transmitter and the RF electromagnetic receiver;
   wherein the transmitted RF signals and received RF signals are coupled into a processor to form a radar system, and
   wherein the processor comprises an operating mode in which the processor is configured to generate a blood pressure dataset based on the received RF signals, said blood pressure dataset containing data pertaining to the user's arterial pulse waveform.

2. The wearable system of claim 1, further comprising an enclosure, wherein the enclosure houses the RF electromagnetic transmitter and the RF electromagnetic receiver.

3. The wearable system of claim 1, further comprising a guiding structure to influence at least one property of the received reflected RF signals.

4. The wearable system of claim 1, wherein a guiding structure is arranged between at least one of the group consisting of: the RF electromagnetic transmitter and the target body region, the RF electromagnetic receiver and the target body region, or both of the RF electromagnetic transmitter and receiver and the target body region.

5. The wearable system of claim 1, further comprising a calibration sensor that measures at least one cardiovascular parameter of the user, wherein the processor comprises: a calibration mode, wherein in the calibration mode the processor is configured to receive a set of input parameters based on the measured at least one cardiovascular parameter of the user from the calibration sensor, and wherein in the calibration mode the processor is configured to output a set of calibration parameters.

6. The wearable system of claim 5 wherein in the operating mode the processor is configured to generate the blood pressure dataset based on the received reflected RF signals and the set of calibration parameters.

7. The wearable system of claim 1, wherein the system further comprises an activity sensor for detecting motion of the wearable system, and the system is configured to determine whether a detected motion level of the wearable system is below a threshold motion level prior to triggering operation of the system to measure the user's arterial pulse waveform.

8. The wearable system of claim 1, wherein the system further comprises an activity sensor for detecting an activity state of the user, and wherein the processor is configured to generate a contextualized blood pressure dataset based on the activity state of the user.

9. The wearable system of claim 1, wherein the radar system is a frequency modulated continuous wave radar system.

10. The wearable system of claim 1, wherein the radar system is a doppler radar system.

11. The wearable system of claim 1, wherein the radar system is a pulsed radar system.

12. The system of claim 1, wherein the standoff distance for the RF electromagnetic transmitter is different from the stand-off distance for the RF electromagnetic receiver.

13. The wearable system of claim 1, wherein the standoff mechanism comprises a curved shape.

14. The wearable system of claim 1, wherein the processor is wearable along with the other components of the wearable system.

15. The wearable system of claim 1, wherein the standoff distance from the user's skin is within a range of between 4 mm and 10 mm for each of the RF electromagnetic transmitter and the RF electromagnetic receiver.

16. The wearable system of claim 1, wherein the standoff mechanism is configured such that the target body region remains outside of the reactive near-field region of the RF electromagnetic transmitter and the RF electromagnetic receiver.

* * * * *